United States Patent [19]

Verkaart

[11] Patent Number: 5,290,237
[45] Date of Patent: Mar. 1, 1994

[54] ORIENTATION-INDEPENDENT DEVICE FOR REMOVAL OF GAS FROM A CELLULAR FLUID

[76] Inventor: Wesley H. Verkaart, 160 Weymouth St., Rockland, Mass. 02370

[21] Appl. No.: 822,010

[22] Filed: Jan. 17, 1992

[51] Int. Cl.⁵ ............................................. A61M 1/00
[52] U.S. Cl. ................................................... 604/126
[58] Field of Search .................. 604/122, 123, 126; 55/158, 159

[56] References Cited

U.S. PATENT DOCUMENTS

| | | | |
|---|---|---|---|
| 3,523,408 | 8/1970 | Rosenberg | 55/159 |
| 3,909,218 | 9/1975 | Kumura et al. | 55/158 |
| 4,293,419 | 10/1981 | Sekino et al. | 55/158 X |
| 4,571,244 | 2/1986 | Knighton | 604/126 X |
| 4,615,694 | 10/1986 | Raines . | |
| 4,640,773 | 2/1987 | Nishida et al. | 55/158 X |
| 4,900,308 | 2/1990 | Verkaart | 604/126 |

FOREIGN PATENT DOCUMENTS 0302722 3/1983 European Pat. Off. .
1959679 11/1969 Fed. Rep. of Germany .
2042919 11/1978 United Kingdom .

*Primary Examiner*—Gene Mancene
*Assistant Examiner*—Jeffrey A. Smith
*Attorney, Agent, or Firm*—Dickinson, Wright, Moon, Van Dusen & Freeman

[57] ABSTRACT

A device for reducing the amount of a gas contained in a liquid includes a central core with an inlet channel, an outlet channel, and a transverse channel. A first chamber is formed on a first side of the core for receiving the liquid from the inlet channel, and a second chamber is formed on the opposite side of the core for receiving the liquid after it has passed through the first chamber. Each of the chambers includes a hydrophobic membrane for allowing gas that has separated from the liquid to pass to the atmosphere. The two chambers are arranged such that gas escaping from the liquid rises to the top of at least one of the chambers for any orientation of the device. The device, accordingly, is not dependent on orientation for effectiveness.

9 Claims, 4 Drawing Sheets

ORIENTATION-INDEPENDENT DEVICE FOR REMOVAL OF GAS FROM A CELLULAR FLUID

TECHNICAL FIELD

This invention relates to the art of devices for removal, or elimination, of a gas from a liquid. In the preferred embodiment, the device is designed to eliminate air from physiological fluids such as blood and crystalloid solutions.

BACKGROUND ART

Physiological fluids that are infused into a patient can contain gasses, such as air or oxygen. The presence of these gasses can arise in various ways, a common one being outgassing resulting from the heating of the fluids.

A known device for elimination of gasses from a physiological fluid is shown in applicant's prior U.S. Pat. No. 4,900,308. This patent describes a gas elimination device, which provides a vertical column through which the fluid flows. The flow of the fluid through the column is such that the gas forms into bubbles, which rise to the top of the column. The gas then passes through a hydrophobic membrane at the top of the column and escapes to the environment.

The device shown in U.S. Pat. No. 4,900,308 is dependent on the orientation of the device because the membrane is located at the end of the column that is intended to be above the opposite end. If the column is inverted, the gas bubbles will rise to the end of the column that does not have provision for allowing escape of the gasses.

Gas elimination devices that are not dependent on the orientation of the device are known. These devices, however, rely on hydrophilic membranes to remove the gas, and these membranes are not useful with the cellular fluids, such as blood, that concern applicant.

SUMMARY OF THE INVENTION

It is often desired to remove gasses from a fluid without regard to the orientation of the gas eliminating device. For example, it may be desired to attach the gas eliminating device to an infusion line receiving fluid from a heat exchanger in such a manner that the line and gas eliminating device are freely movable. If removal of the gas is to be ensured, the operation of a gas elimination device in such an environment must not be dependent on its orientation.

The gas elimination device of the invention is not dependent on the orientation of the device and may be placed almost anywhere in the infusion line downstream of the heat exchanger. The device provides a path for flow of the fluid that includes at least two path sections extending in different respective directions. The flow of the fluid in these sections is such that gas bubbles can rise through the fluid in a direction opposed to the direction of flow of the fluid and thereby separate from the fluid. Because the path sections extend in different directions, there will be at least some part of the path oriented such that the gas bubbles can separate from the fluid for any orientation of the device.

Hydrophobic membranes are located with respect to the path of flow of the fluid such that gas bubbles, which have separated from the liquid, can pass through the membrane and escape to the atmosphere. In the preferred embodiment, the fluid is directed sequentially through first and second chambers. Each of the chambers is formed, at least partially, by a respective one of the membranes whereby the gas separated from the fluid is efficiently discharged to the atmosphere. The chambers are formed on opposed sides of a central body, and the fluid is supplied to the chambers through passages in the body.

Gas passing through the membranes is directed to outlet passages that include one-way valves to prevent the reverse flow of air into the fluid.

BRIEF DESCRIPTION OF THE DRAWINGS

FIG. 4a is a cross section of the gas eliminator of FIG. 4 taken along line 4a—4a.

FIG. 5a is a transverse cross section of the gas eliminator of FIG. 5 taken along line 5a—5a.

FIG. 6a is a transverse cross section of the gas eliminator of FIG. 6 taken along line 6a—6a.

DETAILED DESCRIPTION OF THE PREFERRED EMBODIMENT

Figure 1:
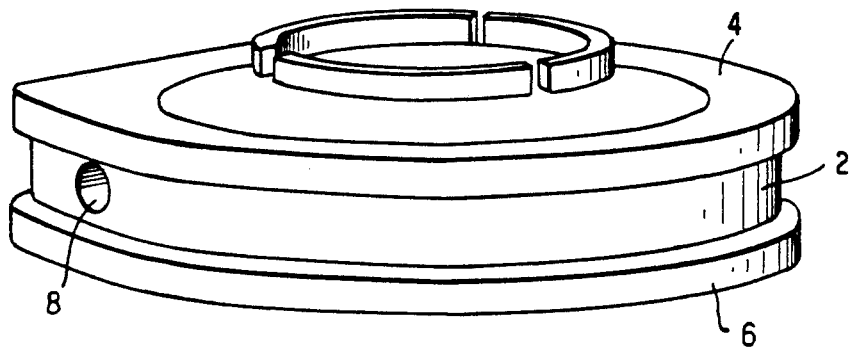
FIG. 1 is a perspective view of a gas eliminator in accordance with the invention.
Figure 2:
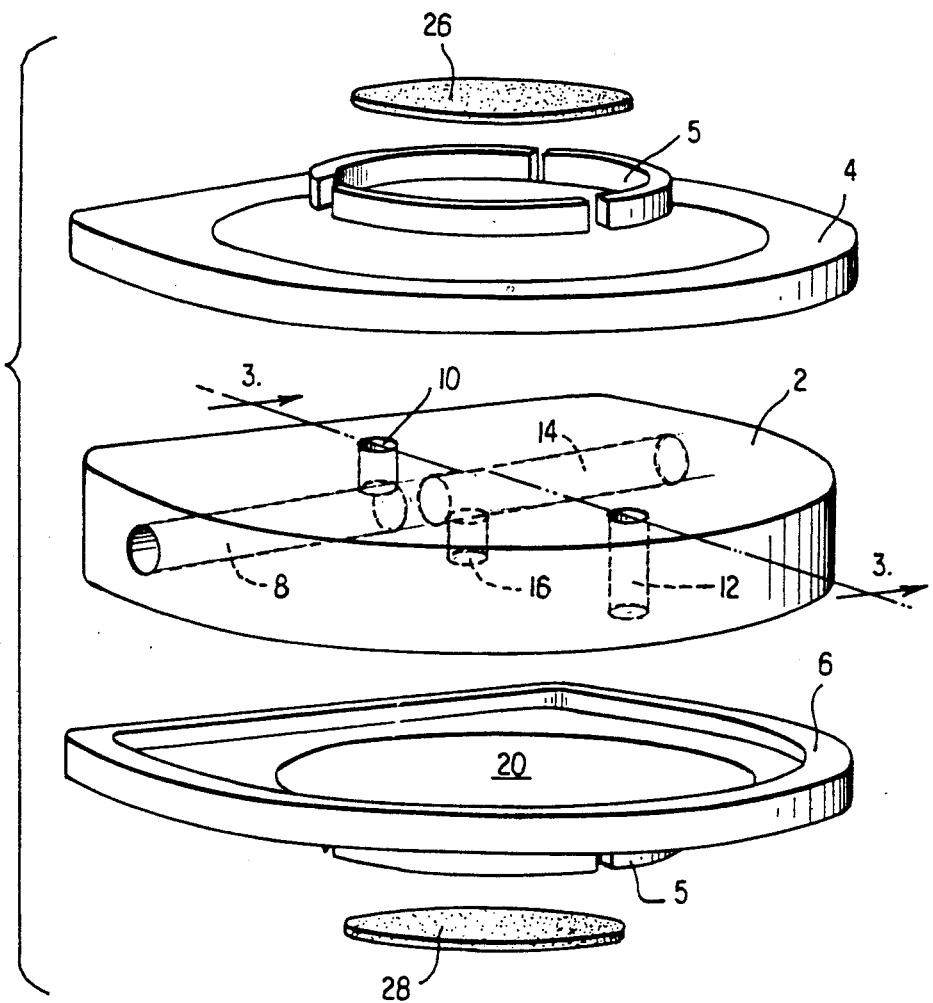
FIG. 2 is an exploded view of the gas eliminator shown in FIG. 1.

With reference to FIG. 1 of the drawings, a gas eliminator in accordance with the invention comprises a central core 2 located between two filter frames, 4 and 6. These parts are preferably made of molded plastic and ultrasonically welded to each other. As illustrated in FIG. 2, the core 2 provides an inlet channel 8 for receiving fluid from, for example, an infusion line. The inlet channel 8 may have a female luer fitting (not shown) attached thereto for facilitating attachment to the infusion line. The inlet channel 8 terminates in an opening 10, which discharges fluid into one end of a first gas elimination chamber as will be more fully explained with reference to other figures. A transverse channel 12 extends through core 2 from an opposite end of the first chamber and carries fluid from the first chamber into a first end of a second gas elimination chamber. An outlet channel 14 receives fluid from an opposite end of the second chamber through opening 16 for discharge of the degassed fluid. A male luer fitting (not shown) may be attached to the outlet channel 14.

Figure 3:
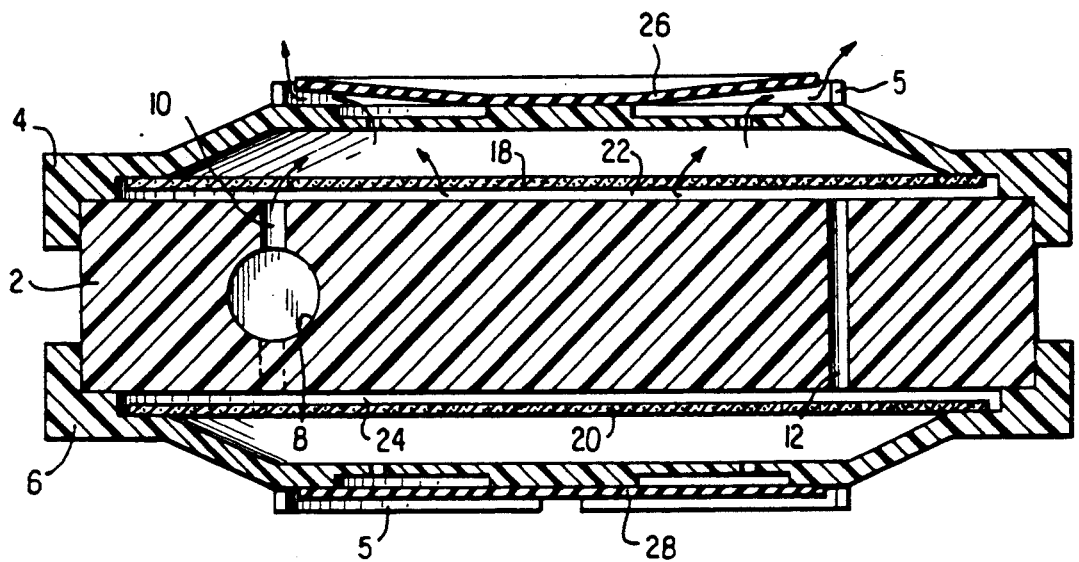
FIG. 3 is a transverse cross section of the gas eliminator of FIGS. 1 and 2 along line 3—3 of FIG. 2 and in a first orientation.

With reference to FIG. 3, each of the filter frames 4 and 6 carries a respective hydrophobic filter membrane 18 and 20. Membrane 18 forms a chamber 22 between the membrane and a surface of the core 2. Similarly, a chamber 24 is formed between membrane 20 and the opposite side of the core 2. Filter frame 4 supports a first one-way valve 26, and filter frame 6 supports a second one-valve 28. These valves prevent the reverse flow of air into the chambers should the pressure in the chambers be reduced. The one-way valves include discs of flexible material, and walls 5 form protective recesses for these.

An important feature of the invention is that it is capable of separating gas from a fluid and discharging the gas to the atmosphere irrespective of the orientation of the gas eliminator. FIGS. 3 through 6 illustrate the gas eliminator in a variety of orientations for describing how it operates to accomplish this purpose.

FIG. 3 illustrates the operation when the gas eliminator is oriented such that the filter frame 4 is horizontal and above filter frame 6. In this position, chamber 22 extends generally horizontally and is filled with liquid flowing from opening 10 to transverse channel 12. The gas in the liquid naturally forms bubbles, which rise to the upper part of the chamber as illustrated by the arrows in FIG. 3. The gas passes through membrane 18 and through one-way valve 26 to be discharged to the atmosphere. The liquid from which the gas has been allowed to escape flows through transverse channel 12, chamber 24, and outlet channel 14 to be directed to an infusion line.

The removal of gas when the gas eliminator is in the orientation wherein filter frame 6 is on the top (i.e., the gas eliminator shown in FIG. 3 turned over) is similar to that described with respect to FIG. 3. The gas will separate from the liquid in chamber 24, and the gas will pass through membrane 20 and one-way valve 28.

Figure 4:
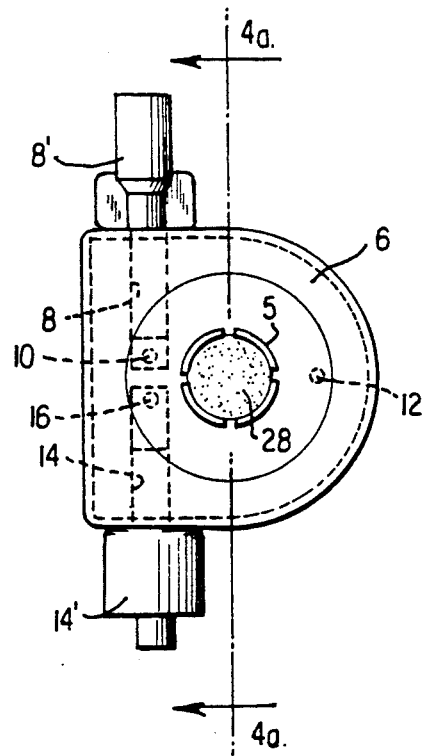
FIG. 4 is a side elevation view of the gas eliminator of FIG. 1 in a second orientation.
Figure 4A:
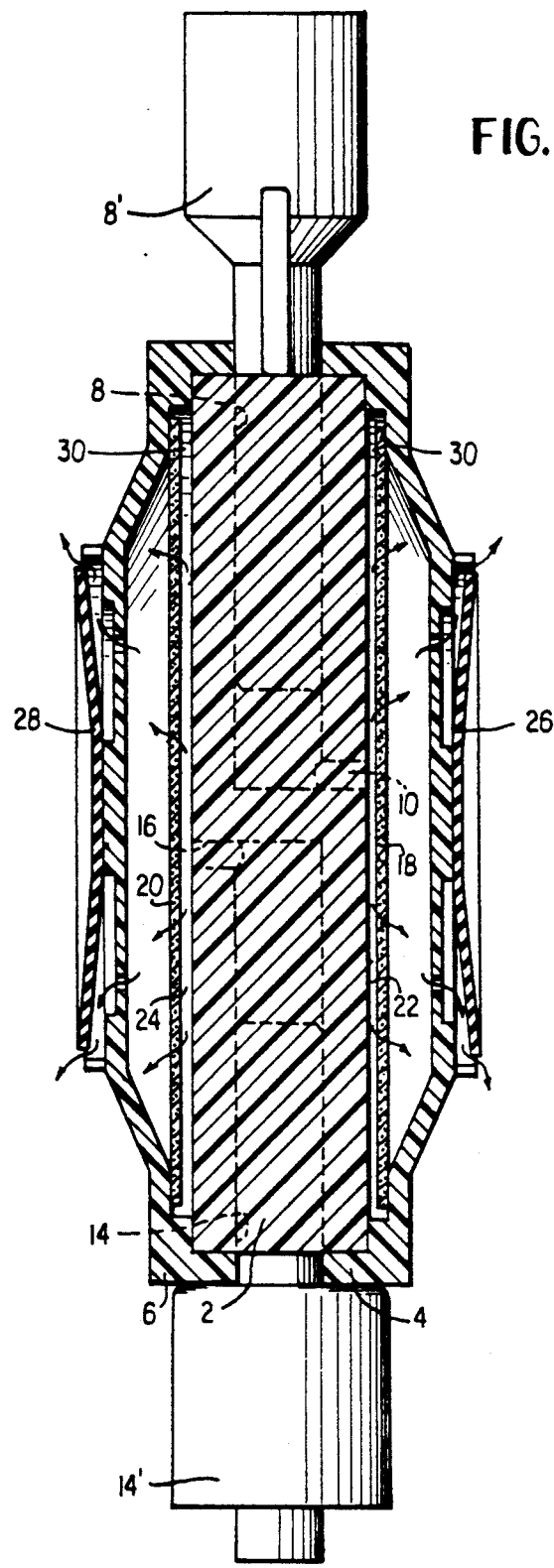
Figure 5:
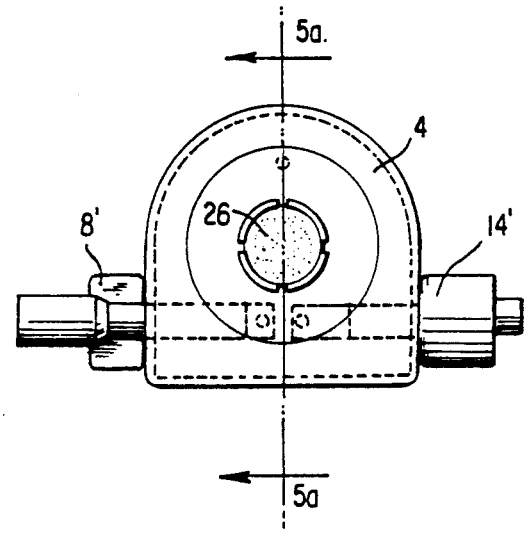
FIG. 5 is a side elevation of the gas eliminator of FIG. in a third orientation.
Figure 6:
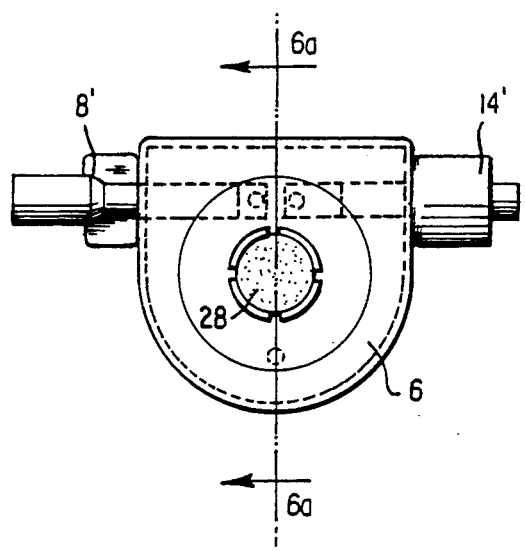
FIG. 6 is side elevation of the gas eliminator of FIG. 1 in a fourth orientation.

FIGS. 4 and 4a illustrate the operation of the device when the inlet channel 8 is at the top, as if the device were hanging from the inlet line. In FIGS. 4, 5, and 6, the inlet luer fitting is designated 8', and the outlet luer fitting is designated 14'. In the orientation of FIG. 4, the gas will separate from the liquid and rise to the top of chambers 22 and 24 as the liquid flows through these chambers. Some of the gas will separate from the liquid in each of the chambers and will accumulate at the upper portions of the chambers as illustrated at 30. The gas will then pass through the upper parts of the membranes 18 and 20 and pass to the atmosphere through the one-way valves.

A similar operation will take place when the outlet 14 is above the inlet 8 with the air bubbles forming at the ends of the chambers 22 and 24 adjacent the outlet 14.

Figure 5A:
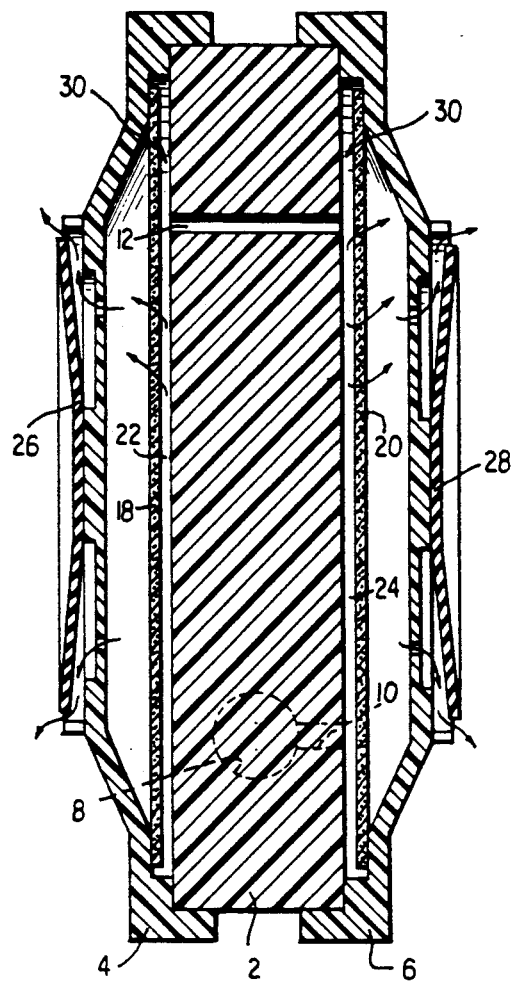

FIGS. 5 and 5a illustrate the operation of the gas eliminator when the inlet and outlet extend horizontally and transverse channel 12 is above the inlet 8. In this orientation, the primary separation of the gas occurs when the liquid is flowing from transverse channel 12 to the outlet because the gas rises counter current to the flow of the liquid. Thus, most of the gas accumulates in the upper region 30 of the chamber 24 and exits through the upper part of the membrane 20. Gas may separate from the liquid in chamber 22, and this gas will accumulate at upper region 30 of chamber 22 and pass through membrane 18 and exit to the atmosphere by one-way valve 26.

Figure 6A:
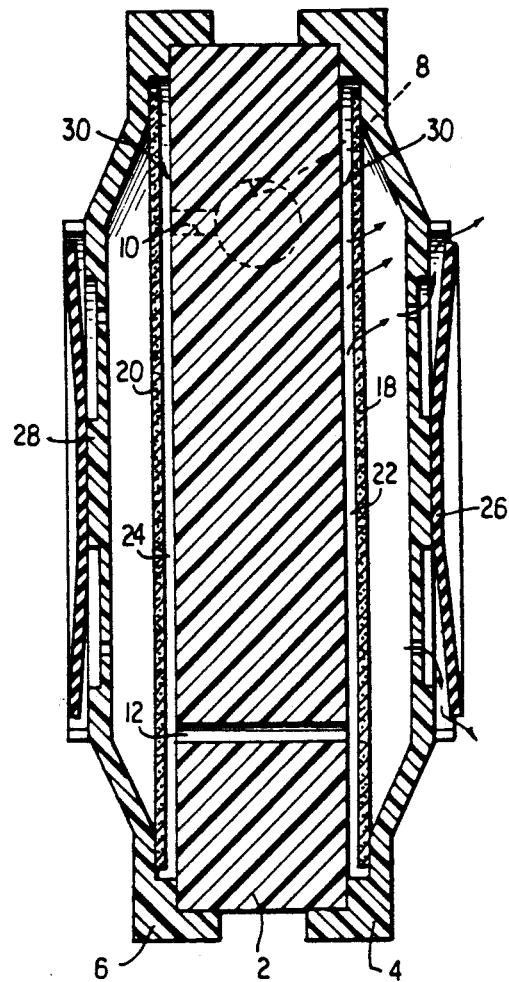

FIGS. 6 and 6a illustrate the situation where the gas eliminator is oriented such that the inlet and outlet extend horizontally and the inlet 8 is above the transverse channel 12. In this orientation, the major part of the separation of the gas from the liquid will occur when the liquid flows from inlet channel 8 to the transverse channel 12. This gas will accumulate in the upper part 30 of chamber 22 and pass through membrane 18. Gas separated from the liquid in chamber 24 will accumulate in upper region 30 and pass to the atmosphere through membrane 20.

In either of the orientations shown in FIGS. 5 and 6, gas passing from one chamber to the other by way of transverse channel 12, for example by entrainment with the liquid flow, will rise to the top of the other chamber and pass through the respective membrane.

Because other orientations are combinations of those that have been described, it will be appreciated that a unique gas eliminator, which is independent of orientation, has been disclosed. Modifications within the scope of the appended claims will be apparent to those of skill in this art.

I claim:

1. Orientation independent apparatus for reducing the amount of a gas contained in a cellular fluid comprising:
   a central core having inlet means for receiving said fluid having said gas therein,
   first chamber means on a first side of said core for receiving said fluid from said inlet means and allowing said gas to form bubbles and to separate from said fluid by rising with respect to said fluid,
   first gas elimination means including a gas permeable membrane on said first side of said core for allowing gas separated from said fluid in said first chamber means to escape into the atmosphere,
   second chamber means on a second side of said core for receiving said fluid from said first chamber means and allowing said gas to form bubbles and to separate from said fluid by rising with respect to said fluid,
   second gas elimination means including a gas permeable membrane on said second side of said core for allowing gas separated from said fluid in said second chamber means to escape into the atmosphere, and
   outlet means for receiving said fluid from said second chamber means and discharging said fluid.

2. Apparatus according to claim 1 wherein said first side and said second side of said core are oppositely facing.

3. Apparatus according to claim 1 wherein said inlet means comprises an inlet channel for supplying said fluid to one end of said first chamber means, said core comprises a transverse channel at an opposite end of said first chamber means for carrying said fluid from said opposite end of said first chamber means to a first end of said second chamber means, and said outlet means comprises an outlet channel in said core at an opposite end of said second chamber means.

4. Apparatus according to claim 3 wherein said inlet and outlet channels are adjacent each other and remote from said transverse channel.

5. Apparatus according to claim 4 further comprising valve means for preventing flow of gas into either of said first chamber means and said second chamber means.

6. Apparatus according to claim 5 wherein said valve means comprises a first one-way valve for receiving gas escaping from said first chamber means and a second one-way valve for receiving gas escaping from said second chamber means.

7. Apparatus according to claim 1 wherein each of said first and second gas elimination means comprises an hydrophobic membrane.

8. Apparatus for separating gas from a fluid comprising a first gas separation chamber that depends on orientation for proper operation for allowing gas separated from said fluid to exit from said first gas separation chamber, a second gas separation chamber that depends on orientation for proper operation for allowing gas separated from said fluid to exit from said second gas separation chamber, means for connecting said first and second gas separation chambers such that the orientation of said first gas separation chamber is different from the orientation of said second gas separation chamber for any orientation of said first gas separation chamber, and means for supplying said fluid to an inlet of said first gas separation chamber and for passing said fluid from an outlet of said first gas separation chamber to an inlet of said second gas separation chamber.

9. Apparatus according to claim 8 wherein said fluid is a cellular fluid and each of said first and second gas separation chambers comprises a hydrophobic membrane.

* * * * *